(12) United States Patent
Chunglo

(10) Patent No.: US 9,645,063 B2
(45) Date of Patent: May 9, 2017

(54) APPARATUS AND PROCESS FOR MEASURING VISCOELASTIC FOAM COMPRESSION RECOVERY

(71) Applicant: Dreamwell, Ltd., Las Vegas, NV (US)

(72) Inventor: Christopher F. Chunglo, Marietta, GA (US)

(73) Assignee: DREAMWELL, LTD., Las Vegas, NV (US)

( * ) Notice: Subject to any disclaimer, the term of this patent is extended or adjusted under 35 U.S.C. 154(b) by 182 days.

(21) Appl. No.: 14/716,202

(22) Filed: May 19, 2015

(65) Prior Publication Data
US 2016/0341642 A1    Nov. 24, 2016

(51) Int. Cl.
*G01N 3/08* (2006.01)

(52) U.S. Cl.
CPC ....... *G01N 3/08* (2013.01); *G01N 2203/0019* (2013.01); *G01N 2203/0085* (2013.01); *G01N 2203/0094* (2013.01)

(58) Field of Classification Search
CPC ............. G01N 3/08; G01N 2203/0094; G01N 2203/0085; G01N 2203/0019
USPC ... 73/818, 790, 806, 816, 825, 79, 82, 11.04
See application file for complete search history.

(56) References Cited

U.S. PATENT DOCUMENTS

| | | | |
|---|---|---|---|
| 5,090,249 A * | 2/1992 | Bielewicz | G01N 3/08 73/822 |
| 5,789,681 A * | 8/1998 | Angley | G01N 3/42 73/803 |
| 6,668,662 B2 * | 12/2003 | Isogai | G01N 3/56 73/790 |
| 7,878,987 B2 * | 2/2011 | Hansma | A61B 5/4504 600/587 |
| 8,398,568 B2 * | 3/2013 | Hansma | A61B 5/4504 600/587 |
| 8,766,811 B2 * | 7/2014 | Spampinato | G01N 3/08 340/665 |
| 9,395,288 B2 * | 7/2016 | Wolkin | G01N 3/32 |
| 2002/0007682 A1 * | 1/2002 | Arimond | G01N 3/08 73/818 |
| 2011/0171354 A1 * | 7/2011 | Funk | G01N 3/08 426/231 |
| 2012/0106804 A1 * | 5/2012 | Canales Compes | G01N 3/08 382/111 |
| 2012/0188088 A1 * | 7/2012 | Spampinato | G01N 3/08 340/665 |
| 2014/0290377 A1 * | 10/2014 | Spampinato | G01N 3/08 73/813 |

(Continued)

*Primary Examiner* — Jonathan Dunlap
(74) *Attorney, Agent, or Firm* — Cantor Colburn LLP

(57) ABSTRACT

An apparatus and process for measuring recovery rate and total recovery time of viscoelastic foam samples. This apparatus will record the change in height with time to fully define how a viscoelastic foam responds to compression. The process generally includes compressing a compression plate against a surface of the viscoelastic foam sample from a nominal height to a pre-determined compressed height, maintaining the pre-determined compressed height for a period of time; retracting the compression plate at a rate greater than a recovery rate so as to disengage the compression plate from the viscoelastic foam sample, and measuring displacement as a function of time to provide a viscoelastic response profile. Measuring the displacement may be contact based or non-contact based.

23 Claims, 3 Drawing Sheets

(56) References Cited

U.S. PATENT DOCUMENTS

2015/0196132 A1\* 7/2015 Duffy .................. A47C 31/123
73/78

\* cited by examiner

APPARATUS AND PROCESS FOR MEASURING VISCOELASTIC FOAM COMPRESSION RECOVERY

BACKGROUND

The present disclosure generally relates to a process for measuring and quantifying viscoelastic foam compression recovery times.

Flexible, viscoelastic polyurethane foam (also known as "slow recovery" foam, "memory" foam or "high damping" foam) is characterized by slow, gradual recovery from compression. While most of the physical properties of viscoelastic foams resemble those of conventional foams, the resilience of viscoelastic foams is much lower, generally less than about 15%. Suitable applications for viscoelastic foam take advantage of its shape conforming, energy attenuating and sound damping characteristics. For example, the foam can be used in mattresses to reduce pressure points, in athletic padding or helmets as a shock absorber, and in automotive interiors for soundproofing.

Currently, ASTM D3574 is available for measuring and categorizing various characteristics of urethane foam materials. Test M of the standard is directed to the measurement of total compression recovery time. In that measurement, a predetermined load is applied via a compression plate to the foam for a fixed amount of time, typically resulting in a significant indentation. Typically, the foam is compressed to 25% of its original height. The compression plate is then retracted to the original height and total recovery time, in seconds, is recorded once the foam contacts the compression plate, which corresponds to the original height.

However, one of the problems with testing viscoelastic foams in this manner is what is currently being referred to as "finger nailing". Finger nailing is a phenomenon that has been observed during compression testing of viscoelastic foams where recovery to the original height is not constant. That is, recovery about a relatively shallow indentation caused by the contact with the compression plate is delayed for an extended period time whereas the bulk recovery of the compression to the finger nailing region can be relatively constant. As a result, the current test processes can result in an inaccurate total recovery time. For example, toluene diisocyanate (TDI) derived viscoelastic foams undergoing compression testing in accordance with D3574, test M, have been observed to recover to its original height at 16 seconds or longer whereas the bulk recovery time is about 3 to 4 seconds. To an end user, this discrepancy is significant and is directly related to feel. The feel experienced by the end user would be that of a viscoelastic foam having a relatively fast recovery time since that is how the bulk of the viscoelastic material behaved, which is markedly different compared to viscoelastic foam having a constant recovery time from the compressed thickness all the way back to the original height, which would have a somewhat softer feel even though total recovery times are substantially identical. Because of this potential for error in total recovery time, the current testing methodology makes it difficult to compare viscoelastic foams with any degree of accuracy. The small impression experienced by some types of viscoelastic foam around the compression plate tricks the ASTM methodology into believing the foam is still recovering.

Moreover, current ASTM testing methodology is generally limited by the time it takes for the compression plate to retract. Useful information below 3 seconds using current ASTM methodology is difficult to obtain. The ASTM retraction rate is such that it takes the compression plate after compression to the compressed height about 3 seconds or more to retract. This prevents accurate measurements for viscoelastic foam materials with response times less than 3 seconds.

Finally, current foam compression testing methodology does not measure the response path. Instead, the compression test simply provides a value for total recovery time after compression at 25 percent of original thickness for a defined amount of time before release of the compression plate. Total recovery time is recorded once the foam reaches the original height and contacts the compression plate. There is no indication as to whether the recovery response was linear or non-linear.

BRIEF SUMMARY

Disclosed herein are apparatuses and processes for measuring recovery rate and recovery time of a viscoelastic foam material.

In one embodiment, the apparatus comprises a support surface configured to receive the viscoelastic foam material; a piston slidably seated inside a cylinder having one end coupled to a compression plate, wherein the piston is configured to compress the compression plate against or retract from a surface of the viscoelastic foam sample, wherein the compression plate comprises at least one aperture; and a sensor disposed above the compression plate configured to continuously measure a height of the viscoelastic foam sample upon retraction of the compression plate, wherein the sensor is configured to have a direct line of sight to the viscoelastic foam material via the at least one aperture.

In another embodiment, the apparatus comprises a support surface configured to receive the viscoelastic foam sample; a piston slidably seated inside a cylinder having one end coupled to a compression plate, wherein the piston is configured to compress the compression plate against or retract from a surface of the viscoelastic foam sample, wherein the compression plate comprises at least one aperture; and a rod slidably engaged with the at least one aperture, wherein the rod has one end coupled to a platen configured to contact, without compression, a surface of the viscoelastic foam sample and another end in electrical communication with an encoder to record displacement of the rod upon retraction of the compression plate from the surface of the viscoelastic foam sample.

A process comprises for measuring recovery rate of a viscoelastic foam sample, wherein the viscoelastic foam sample has a nominal height comprises slidably engaging a rod in at least one aperture of a compression plate, wherein the rod has one end comprising a measurement platen resting on the viscoelastic foam without a load and another end coupled to an encoder; compressing the compression plate against a surface of a viscoelastic foam from the nominal height to a pre-determined compressed height; maintaining the predetermined compressed height for a period of time; retracting the compression plate at a rate faster than a recovery rate for the viscoelastic foam such that the compression plate is completely disengaged from the viscoelastic foam; and recording a recovery rate by the displacement of the measurement platen by the encoder.

In another embodiment, the process comprises aligning a power beam from a laser displacement sensor through at least one aperture of a compression plate and onto a surface of the viscoelastic foam sample; compressing the compression plate against a surface of a viscoelastic foam from the nominal height to a pre-determined compressed height; maintaining the predetermined compressed height for a period of time; retracting the compression plate at a rate faster than a recovery rate for the viscoelastic foam such that the compression plate is completely disengaged from the viscoelastic foam; and recording a recovery rate by the displacement measured by the laser displacement sensor.

The disclosure may be understood more readily by reference to the following detailed description of the various features of the disclosure and the examples included therein.

BRIEF DESCRIPTION OF THE SEVERAL VIEWS OF THE DRAWINGS

Referring now to the figures wherein the like elements are numbered alike.

DETAILED DESCRIPTION

Disclosed herein are apparatuses and processes for measuring and quantifying the recovery rate as a function of time from the compression testing of viscoelastic foam materials. The apparatus and process for measuring and quantifying the recovery rate generally includes compressing a foam sample of the viscoelastic foam between a compression plate and a stationary support, retracting the compression plate by disengaging the compression plate from the surface of the viscoelastic foam; and measuring the recovery rate as a function of time. As will be discussed in greater detail below, measuring the recovery rate may be contact based or non-contact based. The apparatus and process are suitable for testing all types of viscoelastic foam materials.

The apparatus generally includes a compression plate that compresses the viscoelastic foam sample resting on a support surface from its original uncompressed height, i.e., nominal height, to a compressed height, which is a fraction of its nominal height. By way of example, 75 percent compression can be utilized, wherein the viscoelastic foam sample is compressed to 25 percent of its nominal height. The face of the compression surface is then rapidly removed so as to completely disengage contact with the underlying foam surface, and a recovery rate is then generated by a contact or a non-contact configuration, which will be further described below. The recovery rate may be linear and/or non-linear depending on the viscoelastic foam properties and provides a more accurate measurement of the overall feel of the viscoelastic foam instead of relying on total recovery time, which as discussed above in the background section, can be inaccurate due to the finger-nailing phenomena generally associated with testing different types of viscoelastic foam materials.

Figure 1A:
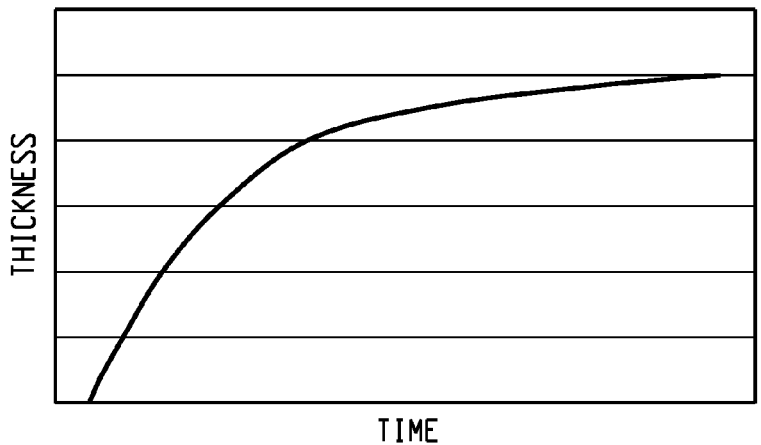
FIG. 1A graphically illustrates foam thickness as a function of compression recovery time for a prophetic example of a viscoelastic foam layer exhibiting a relatively fast compression recovery time.
Figure 1B:
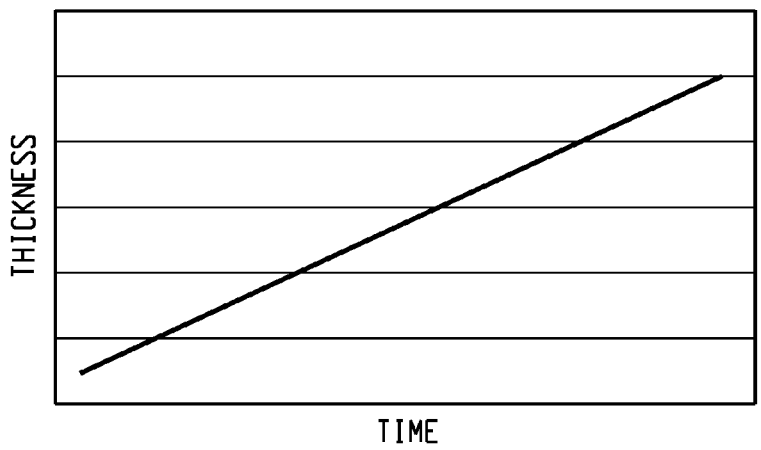
FIG. 1B graphically illustrates foam thickness as a function of compression recovery time for a prophetic example of a viscoelastic foam layer exhibiting a linear compression recovery time.
Figure 1C:
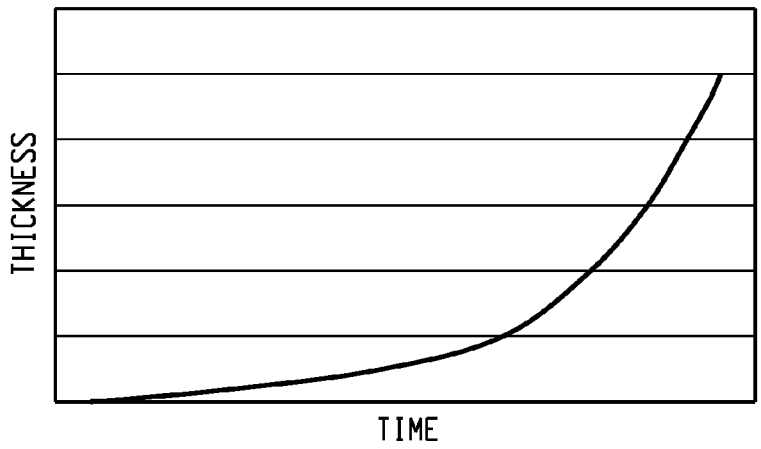
FIG. 1C graphically illustrates foam thickness as a function of compression recovery time for a prophetic example of a viscoelastic foam layer exhibiting a relatively slow compression recovery time.

By way of example of the value associated with the apparatus and process in accordance with the present disclosure, FIGS. 1A-C provide prophetic recovery rates in graphical form as a function of compressed foam height as a function of time representative of viscoelastic foams having different recovery rates with the same total recovery time. The recovery rates, also referred to herein as a viscoelastic response profile, can provide insight to an end user as to the overall feel characteristics of the viscoelastic foam.

FIG. 1A graphically illustrates a non-linear recovery rate indicative of a viscoelastic foam having the least amount of viscoelastic "feel" compared to viscoelastic foams having the response curves shown in FIGS. 1B and 1C. As shown, once the compression plate is disengaged from the surface of the viscoelastic foam being tested, recovery is fast over a relatively short period of time until the remaining compression approximates the original thickness or height. The fast response would be indicative of a foam that did not have as much of a viscoelastic foam feel compared to a viscoelastic film having a slower response time.

In FIG. 1B, the recovery rate is essentially linear throughout the recovery time, which may be indicative of viscoelastic foam having a good feel.

In FIG. 1C, the recovery rate, like FIG. 1A is also non-linear but the recovery rate is significant slower throughout the recovery time, which would provide an end user with a "gooey" like feel. That is, the end user would "sink" into the viscoelastic foam and the imprint resulting from the compression caused by the end user would slowly recover to the original height, which would likely make it difficult for the end user to shift from one position to the next if the viscoelastic foam layer were utilized in a mattress setting.

Figure 2:
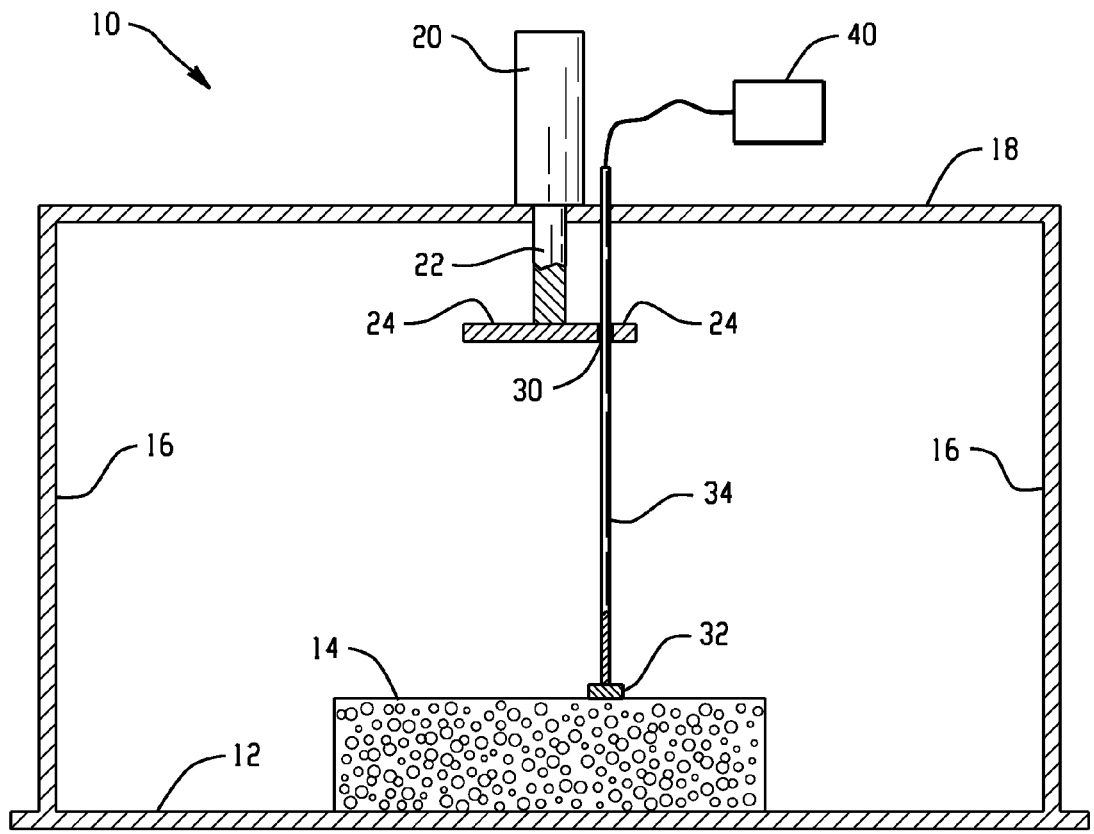
FIG. 2 is a side view of an apparatus configured for contact measurement of the recovery rate and recovery time in accordance with the present disclosure.

Turning now to FIG. 2, there is depicted an apparatus 10 suitable for use for measuring the recovery rate and total recovery time of viscoelastic foam materials. The apparatus 10 includes a support surface 12 upon which a viscoelastic foam block 14 is placed during testing. This surface can be ventilated to allow air to flow in and out of the foam sample 14 during the test. Upright support members 16 extend from the support surface 12 and support cross member 18 is carried between support members 16. The three dimensional overall shape provided by the various members is rectangular or square shape. A cylinder 20 is coupled to a cross member 18 and centrally located above the support surface 12. The cylinder 20 includes a movable piston 22 having a compression plate 24 at an end of the piston, e.g., a test platen of a defined dimension can be used, which may be flat or ventilated. The cylinder 20 is configured to extend and rapidly retract the compression plate 24 relative to the foam sample. The particular cylinder is not intended to be limited to a particular type so long as the compression plate 24 can be disengaged from contact with the compressed foam surface at about commencement of testing, i.e., at about the time the compression plate is retracted from the foam surface. By way of example, the cylinder can be a hydraulic cylinder, a pneumatic cylinder, or the like. Other mechanisms (not shown) that use linkages or cams coupled to the compression plate may be used and actuated manually, pneumatically, hydraulically or by an electric motor.

Figure 3:
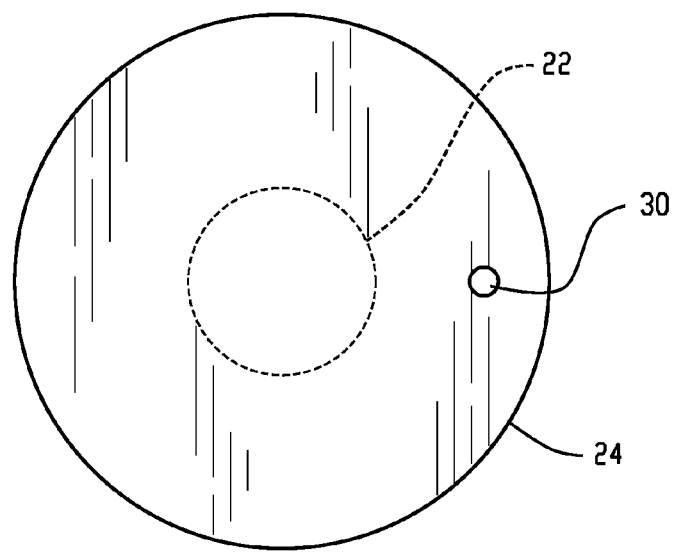
FIG. 3 is a top down view of a compression plate for use in the apparatus of the present disclosure.

As previously discussed, the apparatus 10 can be configured for contact or non-contact for determining the recovery rate. The apparatus 10 shown in FIG. 2 is configured for contact recovery rate measurement, wherein the compression plate 24, i.e., test platen, includes at least one aperture 30 as shown in FIG. 3. Referring back to FIG. 2, the aperture 30 is dimensioned to accommodate measurement platen 32 connected to a rod 34 to pass through the aperture 30 in the compression plate 24. The compression plate 24 would quickly retract and the measurement platen 32, which is slidably engaged within the aperture 30, would ride on top of the viscoelastic foam 14 during recovery. The rod 34 would be connected to an encoder 40 that would record the amount and rate of displacement of the platen 32 during the recovery.

Figure 4:
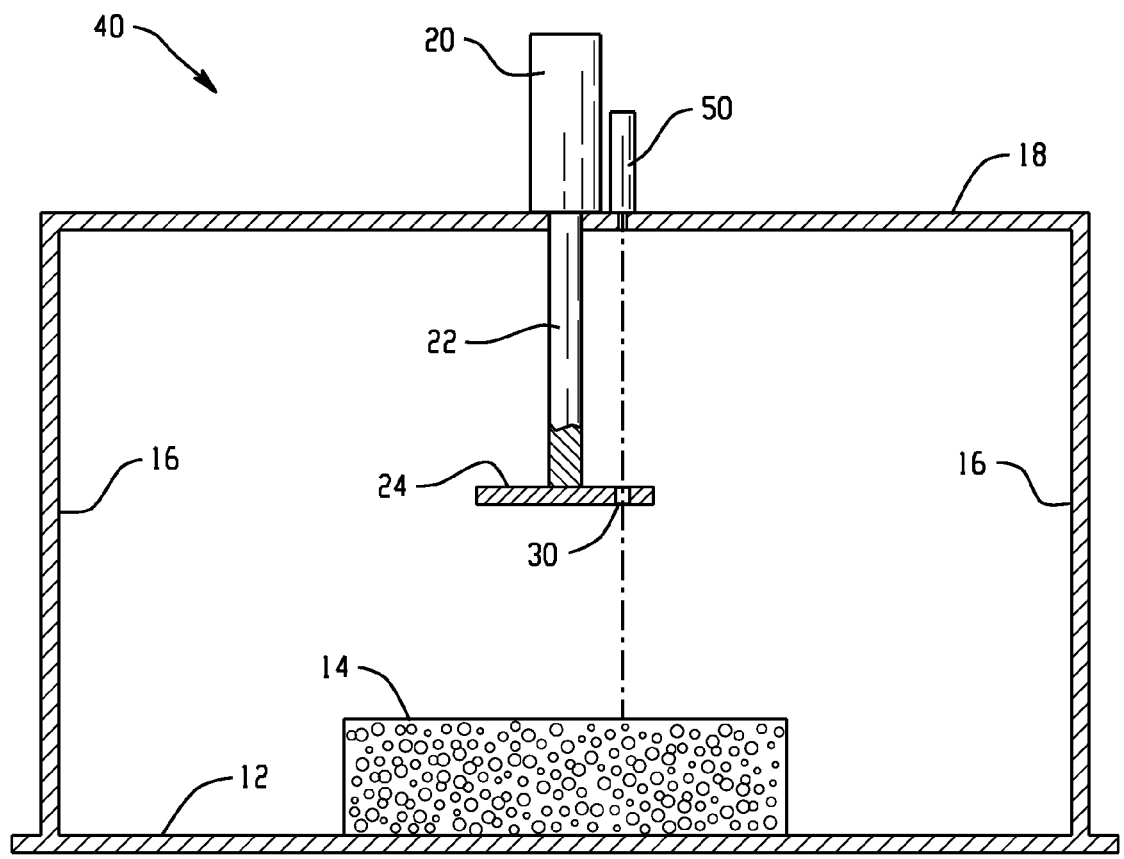
FIG. 4 is a side view of an apparatus configured for non-contact measurement of the recovery rate and recovery time in accordance with another embodiment of the present disclosure.

In FIG. 4, apparatus 40 is configured for non-contact recovery rate measurement. In this embodiment, the apparatus 40 further includes a laser displacement sensor 50 (in place of the measurement platen 32), which can be mounted on cross member 18 and is aligned with the aperture 30 in the compression surface 24. The laser displacement sensor 50 includes a power beam focused onto area of the foam surface to be compressed and records the return time. The aperture 30 in the compression surface 24 is dimensioned to allow the laser power beam to pass through the compression surface and maintain contact throughout the test. In some embodiments, the aperture 30 may be filled with a material transparent top the laser power beam such that the laser power beam will not be attenuated in any substantial amount that would affect measurement capabilities. The use of a transparent material will help maintain a flat compression of the sample. While this is desirable, it is not critical for the test. In still other embodiments, the entire compression surface 24 is formed of a transparent material that would allow the laser power beam to pass through and take a measurement during the test. When the compression surface 24 retracts and disengages from the compressed surface of the viscoelastic foam sample, the laser continuously records the height of the foam. The data is recorded and can be shown in a graphical format. Laser measurement is very accurate and capable of a high sampling rate to capture data.

A further embodiment would be to directly connect a displacement sensor to the compression surface directly above aperture 30. In this embodiment the sensor will move with the platen. This would allow for a wider range of height measuring devices such as ultrasonic measurements. The test would start when compression plate 24 retracts quickly and stops when the surface of the foam sample 14 stops rising towards the sensor. During the retraction process, data could be lost. This could still be advantageous by making it possible to use other sensors such as an ultrasonic sensor. The ultrasonic sensor can average the height over a larger surface area. This could have advantages in some situations.

The displacement laser is not intended to be limited to any particular type. By way of example, the laser can be a triangulation sensor that measures distance by projecting a beam of laser light that creates a spot on the foam target. Reflected light from the surface is viewed at an angle by a CMOS detector array inside the sensor housing and offset from the power beam. The target distance is calculated form the image pixel data using the sensor's microprocessor. An exemplary laser is commercially available under trade name AR700 from Acuity.

The percentage of compression is not intended to be limited and will generally depend on the intended foam application. For example, to simulate how the foam reacts in bedding applications, the percentage of compression is generally greater than 25 percent to as much as 90 percent. In one embodiment, the compression is greater than 50 to 75 percent of the original height. In still other embodiments, the percentage of compression s 75 percent of the original height. For bedding applications, if has been found that a 75% compression for 60 seconds can be used to simulate how the foam will react in most applications.

The process of measuring the recovery rate and total recovery time generally includes proper placement of the viscoelastic foam sample onto the support surface. The support surface may include guide markings to insure consistent and proper placement for a given foam sample. The foam sample is cut to correspond to accommodate the shape of the compression plate. The thickness of the foam sample is irrelevant for the purposes of the determination of the foam recovery rate; however, the thickness of the sample should be such that apparatus can compress the sample a suitable distance and obtain an accurate determination of the foam recovery rate. Once the foam sample is properly positioned, the process includes contacting compression plate 24 with the foam surface at the desired compression percentage for a defined period of time and then rapidly retracted so as to disengage the compression plate from contact with the foam sample at the desired compression percentage and remain disengaged throughout recovery time testing. In one embodiment, the compression plate is maintained at the desired compressed height for a period of time from 2 seconds to about 5 minutes; in other embodiments, from 10 seconds to 3 minutes and in still other embodiments, from 30 seconds to 2 minutes. For example, current ASTM methodology compresses a standard polyurethane foam, for example, for 1 minute before slowly retracting the face of the compress surface compression. The particular amount of time is generally not intended to be limited so long as the time is consistent when comparing one sample of a viscoelastic foam to another sample.

Alternatively, the total recovery time can be determined by taking into account the fingernail effect. For example, total recovery time can be determined by setting the recovered height of the viscoelastic foam sample to be less than the nominal height. In this manner, samples having identical dimensions can be tested and directly compared to one another without any error resulting from the fingernailing effect. By way of example, the recovered height can be arbitrarily set at 99.9 percent or less of the nominal height. In other embodiment, the recovered height can be set at 95 percent or less; and in still other embodiments, the recovered height can be set at 90 percent or less. In this manner, the total recovery time can be extrapolated and eliminate the measurement errors associated with fingernailing.

An alternate way of interpreting the data is to look at the rate of recovery during the test. You can program in a target minimum rate of change, which would generally occur at an end of a compression recovery cycle and is generally representative of the rate of recovery resulting from the decompression of the fingernailing portion of the compressed foam. Desirably, the target should represent a relatively slow rate of change and can be small enough it would start be become qualitatively unperceivable to an end user. This would define the response time that would be meaningful in the end product. The software can be configured to take the output from the laser power beam to continuously calculate the rate of change. The timer would trigger when this target rate has been achieved. This section could be highlighted in the graph of the results so the target can be validated.

The apparatus and process can be modified for any foam sample size. By way of example, current recommended sample sizes utilized in ASTM D3574 is a 15 inch (L) by 15 inch (W)×4 inch (H) foam block.

One advantage of such a configuration is that the compression remains uniform over the surface area of the foam sample, which, in turn, enables more accurate measurement of the recovery rate of the foam. Moreover, by knowing the recovery rate profile, one of skill in the art can select upper and lower control limits on the recovery rate profile to insure a more consistent feel in the foam across different foam samples.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for measuring recovery rate and recovery time of a viscoelastic foam material, the apparatus comprising:
    a support surface configured to receive the viscoelastic foam material;
    a piston slidably seated inside a cylinder having one end coupled to a compression plate, wherein the piston is configured to compress the compression plate against or retract from a surface of the viscoelastic foam sample, wherein the compression plate comprises at least one aperture; and
    a sensor disposed above the compression plate configured to continuously measure a height of the viscoelastic foam sample upon retraction of the compression plate, wherein the sensor is configured to have a direct line of sight to the viscoelastic foam material via the at least one aperture.

2. The apparatus of claim 1, wherein the sensor is a laser displacement sensor having a power beam aligned with the at least one aperture.

3. The apparatus of claim 2, wherein the laser displacement sensor is a triangulation sensor.

4. The apparatus of claim 1, wherein the sensor is a ultrasonic sensor mounted on the compression plate and aligned with the at least one aperture.

5. The apparatus of claim 1, wherein the cylinder comprises a pneumatic cylinder or a hydraulic cylinder.

6. The apparatus of claim 1, wherein the compression plate is configured to disengage from contact with the surface of the viscoelastic foam sample upon retraction.

7. The apparatus of claim 1, wherein the at least one aperture is filled with a material transparent to the laser power beam.

8. The apparatus of claim 7, wherein the compression plate is formed of a material transparent to the laser power beam.

9. An apparatus for measuring recovery rate and recovery time of a viscoelastic foam material, the apparatus comprising:
    a support surface configured to receive the viscoelastic foam sample;
    a piston slidably seated inside a cylinder having one end coupled to a compression plate, wherein the piston is configured to compress the compression plate against or retract from a surface of the viscoelastic foam sample, wherein the compression plate comprises at least one aperture; and
    a rod slidably engaged with the at least one aperture, wherein the rod has one end coupled to a platen configured to contact, without compression, a surface of the viscoelastic foam sample and another end in electrical communication with an encoder to record displacement of the rod upon retraction of the compression plate from the surface of the viscoelastic foam sample.

10. The apparatus of claim 9, wherein the cylinder comprises a pneumatic cylinder or a hydraulic cylinder.

11. The apparatus of claim 10, wherein the compression plate is configured to disengage from contact with the surface of the viscoelastic foam sample upon retraction.

12. A process for measuring recovery rate of a viscoelastic foam sample, wherein the viscoelastic foam sample has a nominal height, the process comprising:
    slidably engaging a rod in at least one aperture of a compression plate, wherein the rod has one end comprising a measurement platen resting on the viscoelastic foam without a load and another end coupled to an encoder;
    compressing the compression plate against a surface of a viscoelastic foam from the nominal height to a predetermined compressed height;
    maintaining the predetermined compressed height for a period of time;
    retracting the compression plate at a rate faster than a recovery rate for the viscoelastic foam such that the compression plate is completely disengaged from the viscoelastic foam; and
    recording a recovery rate by the displacement of the measurement platen by the encoder.

13. The process of claim 12 further comprising setting a trigger point at a trigger height greater than the predetermined compressed height and smaller than the nominal height; and extrapolating the rate of recovery to define a total recovery time.

14. The process of claim 12, wherein the predetermined compressed height is 25 to 90 percent of the nominal height.

15. The process of claim 12, wherein the period of time from 2 seconds to about 5 minutes.

16. The process of claim 12, wherein the trigger height is 95 percent or less than the nominal height.

17. The process of claim 12, further comprising defining a target minimum rate of recovery at an end of a compression recovery cycle and removing data obtained after the target minimum rate of recovery has been reached.

18. A process for measuring recovery rate of a viscoelastic foam sample, wherein the viscoelastic foam sample has a nominal height, the process comprising:
    aligning a power beam from a laser displacement sensor through at least one aperture of a compression plate and onto a surface of the viscoelastic foam sample;
    compressing the compression plate against a surface of a viscoelastic foam from the nominal height to a predetermined compressed height;
    maintaining the predetermined compressed height for a period of time;
    retracting the compression plate at a rate faster than a recovery rate for the viscoelastic foam such that the compression plate is completely disengaged from the viscoelastic foam; and
    recording a recovery rate by the displacement measured by the laser displacement sensor.

19. The process of claim 18, further comprising setting a trigger point at a trigger height greater than the predetermined compressed height and smaller than the nominal height; and extrapolating the rate of recovery to define a total recovery time.

20. The process of claim 18, wherein the predetermined compressed height is 25 to 90 percent of the nominal height.

21. The process of claim 18, wherein the period of time from 2 seconds to about 5 minutes.

22. The process of claim 18, wherein the trigger height is 95 percent or less than the nominal height.

23. The process of claim 18, further comprising defining a target minimum rate of recovery at an end of a compression recovery cycle and removing data obtained after the target minimum rate of recovery has been reached.

\* \* \* \* \*